Jan. 21, 1969 M. L. MEILLAND Plant Pat. 2,857
ROSE PLANT
Filed July 7, 1967
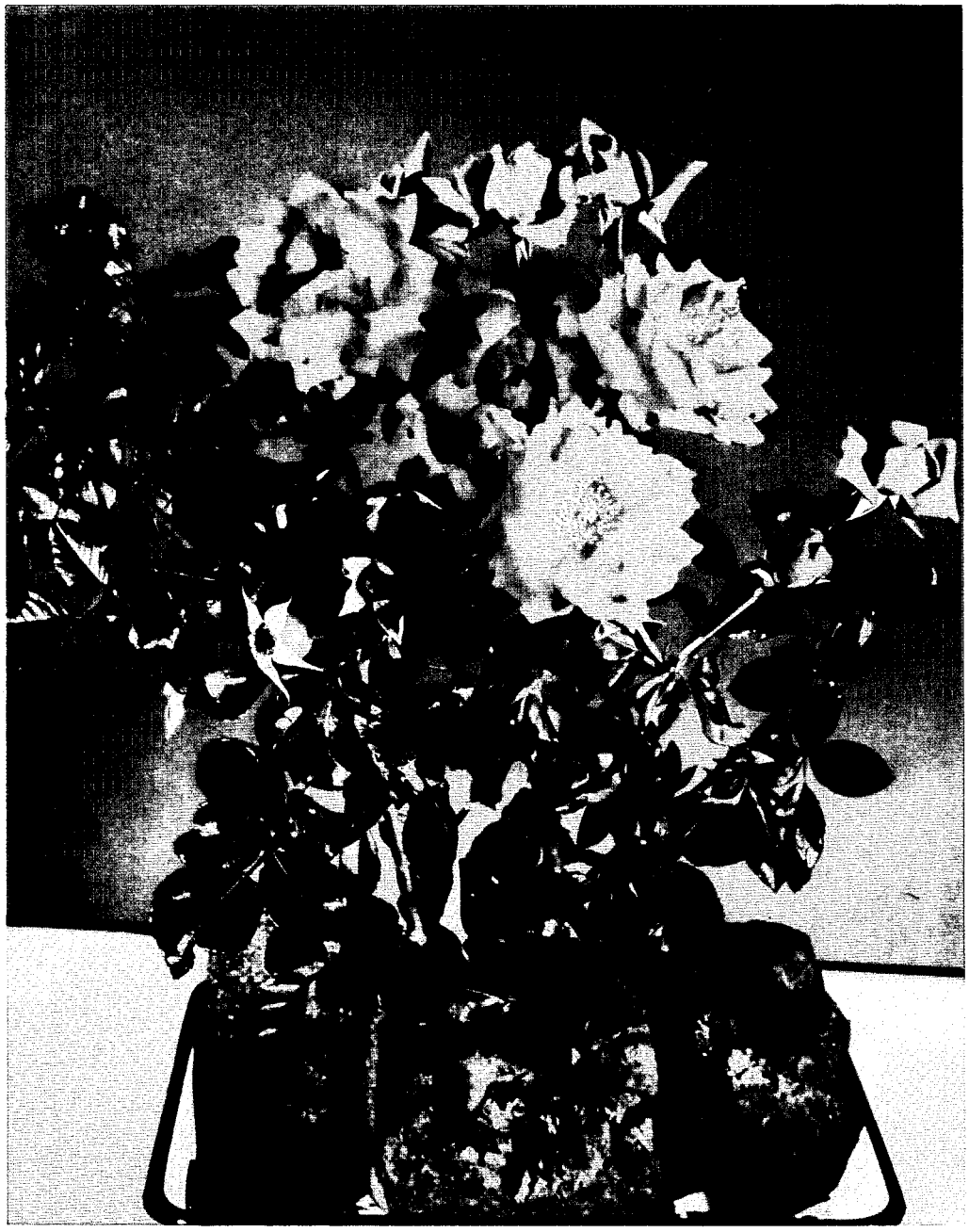
Inventor.
Marie Louise Meilland
By: Robb & Robb
Attorneys.

United States Patent Office

Plant Pat. 2,857
Patented Jan. 21, 1969

2,857
ROSE PLANT

Marie Louise Meilland, Cap d'Antibes, Alpes Maritimes, France

Filed July 7, 1967, Ser. No. 651,961
Claims priority, application France, July 29, 1966, 47,598
U.S. Cl. Plt.—28 1 Claim
Int. Cl. A01h 5/02

The present invention relates to a new and distinct variety of rose plant of the floribunda class, which was originated by me by crossing an unnamed and unpatented rose seedling of "Alain" (unpatented) × *"Rosa mutabilis"* (unpatented) with another unnamed and unpatented seedling of "Radar" (unpatented) × "Caprice" (unpatented), the former seedling being the seed parent, and the latter seedling being the pollen parent.

As the result of this breeding, I have produced a new and improved rose variety which is distinguished from its parents, as well as from all other varieties of which I am aware, as evidenced by the following unique combination of characteristics which are outstanding therein:

(1) A hardy, vigorous, upright, well-branched habit;

(2) Abundant, glossy, attractive Spinach Green foliage which matures to a Parsley Green color, and having average disease resistance;

(3) Abundant, continuous, large clusters of blooms of good size and which have exceptionally long lasting qualities;

(4) A distinctive and attractive flower color ranging between Rose Red and Cherry and which holds up well; and (5) A light tea flower fragrance.

Asexual reproduction of the new variety by budding, as performed in France and also at West Grove, Pa., U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Floribunda.
Breeding: Seedling.
*Seed parent.*—An unnamed seedling of "Alain" × *"Rosa mutabilis."*
*Pollen parent.*—An unnamed seedling of "Radar" × "Caprice."
Propagation: Holds its distinguishing characteristics through succeeding propagations by budding.

*Flower*

Locality where grown and observed: West Grove, Pa., U.S.A.
Flowers borne: From two to several to stem; in irregular clusters; on stems of normal strength and medium to long length.
Quantity of bloom: Abundant, outdoors.
Continuity: Continuous.
Fragrance: Slight. Nature—tea.
Bud:
*Peduncle.*—Medium length; medium caliper; erect; stiff; rough; with medium number of glandular tipped red-brown hairs. Color—green, with reddish overcast.
*Before calyx breaks.*—Size—small. Form—medium length; ovoid; with a conspicuous neck; with foliaceous appendages on the surface of the bud; with slender bristle-like foliaceous parts extending beyond the tip of the bud equal to ¼ or more of its length.
*As calyx breaks.*—Color—Purple Madder, Plate 1028, with blackish markings where first exposed to sunlight.
*As first petal opens.*—Size—from small to medium. Form—medium length; ovoid. Color: outside—area surrounding point of attachment near white, becoming overlaid with Ruby Red, Plate 827 and then irregularly with Maroon, Plate 1030; inside—small area surrounding point of attachment near white, changing sharply to Rose Red, Plate 724, then becoming progressively shaded with Ruby Red, Plate 827 and often with blackish areas toward the margin of the petal.
*Opening.*—Opens up well.
Bloom:
*Size (when fully open).*—Medium; from 3 inches to 3½ inches.
*Petalage.*—Double; from 30 to 35 petals; arranged regularly.
*Form.*—High-centered at first, but becoming open-cupped; petals being at first loosely rolled outward and remaining loosely rolled outward at maturity.
Petals:
*Texture.*—Medium thickness.
*Appearance.*—Inside—velvety. Outside—satiny.
*Shape.*—Outer—obovate. Intermediate—obovate. Inner—undulate.

This description of a newly opened flower was made from a rose grown outdoors during the month of August at West Grove, Pa., U.S.A.:

*Color.*—Outer petal: outside surface—small area surrounding point of attachment near white, changing to Rose Red, Plate 724/3 and progressively to Chrysanthemum Crimson, Plate 824/2; inside surface—small area surrounding point of attachment almost white, changing sharply to between Cherry, Plate 722 and Rose Red, Plate 724, then becoming overlaid with Pansy Purple, Plate 928 in small irregular areas on the margin. Intermediate petal: outside surface—area surrounding point of attachment near white, becoming Rose Red, Plate 724/3 over remainder of petal; inside surface—small area surrounding point of attachment near white, changing sharply to between Cherry, Plate 722 and Rose Red, Plate 824. Inner petal: outside surface—near white at point of attachment and occasionally carried as a streak along the midrib, with remainder of petal China Rose, Plate 024; inside surface—area surrounding point of attachment near white, with a slight yellowish overcast, changing to a tone slightly darker than Cherry, Plate 722 over remainder of petal.

This description was made from a rose that was open for three days outdoors during the month of August at West Grove, Pa., U.S.A.:

*Color.*—Outer petal: outside surface—area surrounding point of attachment near white, becoming progressively Spirea Red, Plate 025/1; inside surface—area surrounding point of attachment near white, changing to a narrow zone of Spirea Red, Plate 025/1, and then progressively shading to Rose Red, Plate 724, overlaid with Cardinal Red, Plate 822 and with blackish shadings when viewed in certain lights. Inner petal: outside surface—base of petal white, becoming Spirea Red, Plate 025/1 and then progressively shading to Chrysanthemum Crimson, Plate 824/2; inside surface—point of attachment near white, changing to Spirea Red, Plate 025/1, and then progressively to Rose Red, Plate 724 overlaid with Cardinal Red, Plate 822, and sometimes with a streak of white following the midrib.

*General color effect.*—Newly opened flower—between Rose Red, Plate 724 and Cherry, Plate 722. Three days open—Rose Red, Plate 724, overlaid with Cardinal Red, Plate 822.

*Behavior.*—Drop off cleanly.

*Flower longevity.*—On bush in garden—five days in August. Cut roses grown outdoors and kept at living room temperatures—four days in August.

*Reproductive organs*

Stamens: Many; arranged regularly about pistils; mixed with petaloids.

Filaments: Most with anthers; from medium to long. Color—yellow, becoming suffused with pink as flower matures.

Anthers: All open at once; medium size; occasionally an anther fused with a petaloid. Color—yellowish.

Pollen: Moderate quantity. Color—gold.

Pistils: Medium number.

Styles: Uneven; from short to medium length; medium caliper; bunched.

Stigma: Color—pale yellow.

Ovaries: All enclosed in receptable.

Hips: Globular; smooth; walls medium dry. Color—green.

Sepals: Permanent; moderately long; spear-shaped.

Seeds: Many; medium size.

*Plant*

Foliage:

*Leaves.*—Compound of 5–7 leaflets; normal abundance; medium size; leathery.

*Leaflets.*—Shape—oval, with apex acute. Base—obtuse. Margin—simply serrate.

*Color.*—Mature: upper surface—Parsley Green, Plate 00962; under surface—Willow Green, Plate 000862. Young: upper surface—Spinach Green, Plate 0960/2, heavily overlaid with Pansy Purple, Plate 928/2; under surface—Lettuce Green, Plate 861/2, overlaid with Pansy Purple, Plate 928/2.

*Rachis (the supporting stem of the compound leaf).*—Medium caliper. Upper side—grooved, with glandular hairs on either margin. Under side—sparsely prickly.

*Stipules.*—Moderately long; narrow; with short points turning out at an angle of less than 45°.

*Disease resistance.*—Comparable to that of the average variety grown under the same cultural conditions at West Grove, Pa., U.S.A.

Growth:

*Habit.*—Bushy; upright; much-branched.

*Growth.*—Vigorous.

*Canes.*—Moderately heavy.

*Main stems.*—Dull. Color—Fern Green, Plate 0862. Prickles—several; color—brown. Hairs—none.

*Branches.*—Dull. Color—Fern Green, Plate 0862. Prickles—several; color—reddish, with yellowish-green points. Hairs—none.

*New shoots.*—Dull. Color—Fern Green, Plate 0862, overlaid with near Pansy Purple, Plate 928/2. Prickles—several; color—reddish. Hairs—none.

I claim:

1. A new and distinct variety of rose plant of the floribunda class, substantially as herein shown and described, characterized particularly as to novelty by the unique combination of a hardy, vigorous, upright, well-branched habit, abundant, glossy, attractive Spinach Green foliage which matures to a Parsley Green color, having average disease resistance, abundant, continuous, large clusters of blooms of good size and which have exceptionally long lasting qualities, a distinctive and attractive flower color ranging between Rose Red and Cherry and which holds up well, and a light tea flower fragrance.

No references cited.

ROBERT E. BAGWILL, *Primary Examiner.*